(12) United States Patent
Bozzarelli

(10) Patent No.: US 9,345,874 B2
(45) Date of Patent: May 24, 2016

(54) PERINEAL PROBE

(71) Applicant: BEACMED S.r.L., Portalbera (Pavia) (IT)

(72) Inventor: Pier Luigi Bozzarelli, Portalbera (IT)

(73) Assignee: BEACMED S.R.L., Portalbera (Pavia) (IT)

( * ) Notice: Subject to any disclaimer, the term of this patent is extended or adjusted under 35 U.S.C. 154(b) by 0 days.

(21) Appl. No.: 14/521,613

(22) Filed: Oct. 23, 2014

(65) Prior Publication Data

US 2016/0114150 A1    Apr. 28, 2016

(51) Int. Cl.
*A61N 1/05*        (2006.01)

(52) U.S. Cl.
CPC ............... *A61N 1/05* (2013.01); *A61N 1/0514* (2013.01); *A61N 1/0524* (2013.01)

(58) Field of Classification Search
CPC ..... A61N 1/05; A61N 1/0514; A61N 1/0524; A61N 1/36; A61N 1/3605; A61N 1/36007
See application file for complete search history.

(56) References Cited

U.S. PATENT DOCUMENTS

| 3,749,100 | A | * | 7/1973 | Von Der Mosel | ............. | 607/138 |
| 6,086,549 | A | * | 7/2000 | Neese et al. | .................. | 600/587 |
| 2005/0228316 | A1 | | 10/2005 | Morgenstern | | |

FOREIGN PATENT DOCUMENTS

| EP | 2 322 110 A1 | 5/2011 |
| WO | 2007/136266 A1 | 11/2007 |
| WO | 2011/159906 A2 | 12/2011 |

OTHER PUBLICATIONS

European Search Report for European Application No. EP 13 15 4151, two pages, completed Jun. 5, 2013.

* cited by examiner

*Primary Examiner* — George Manuel
(74) *Attorney, Agent, or Firm* — Vorys, Sater, Seymour & Pease LLP

(57) ABSTRACT

Provided is a perineal probe including a main axis coinciding with the direction of insertion of said probe and a main body, the main body including: a lower surface, an upper surface, opposite said lower surface, a lateral surface, extending between the lower surface and the upper surface and including two opposite main portions substantially parallel to the main axis, at least two lower electrodes, arranged on the lower surface and reciprocally separated along said main axis, at least two lateral electrodes arranged along said main portions of said lateral surface.

10 Claims, 4 Drawing Sheets

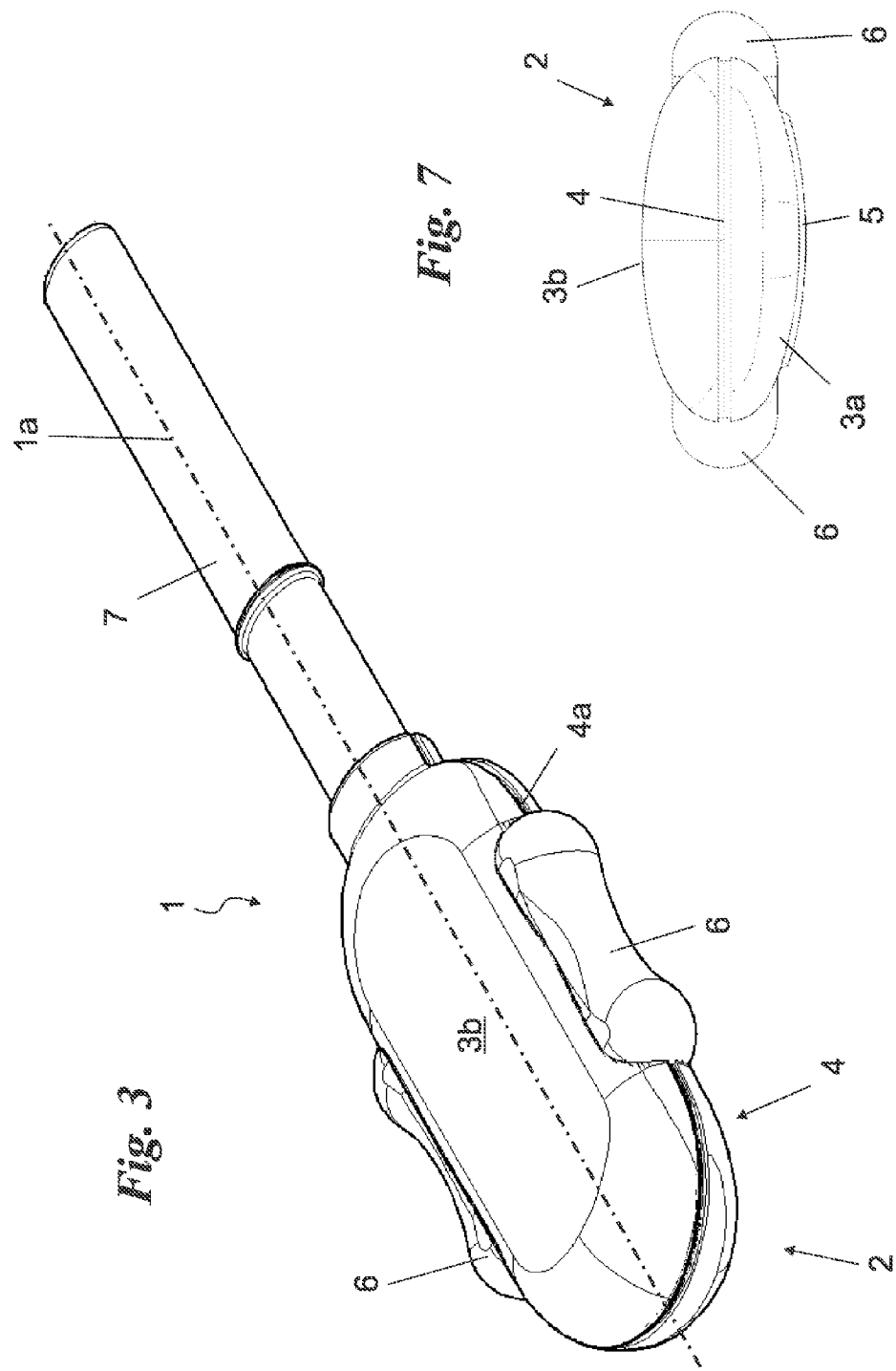

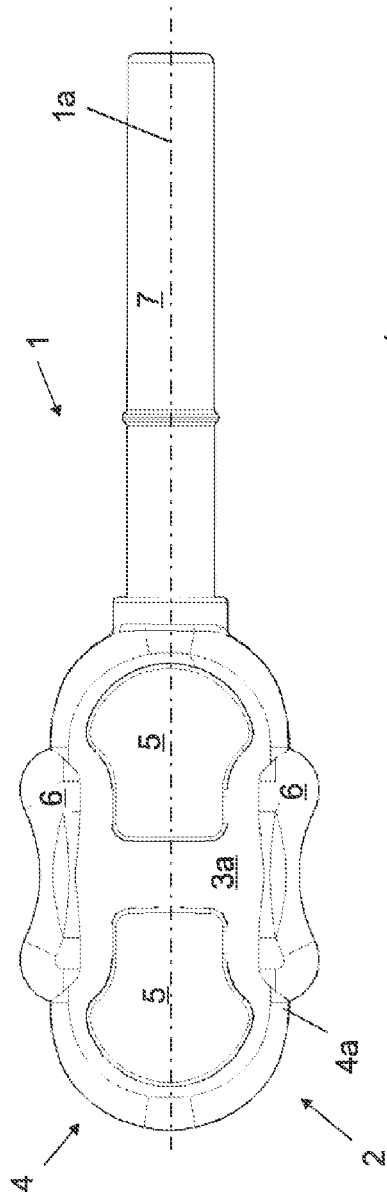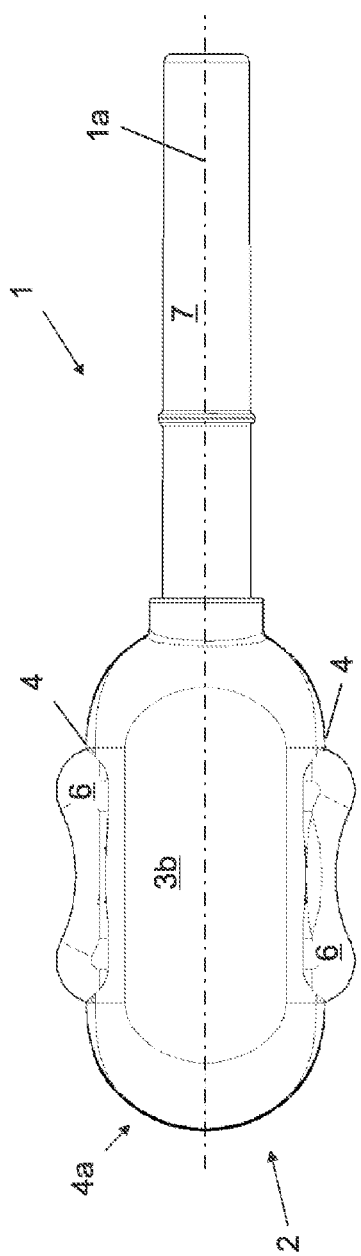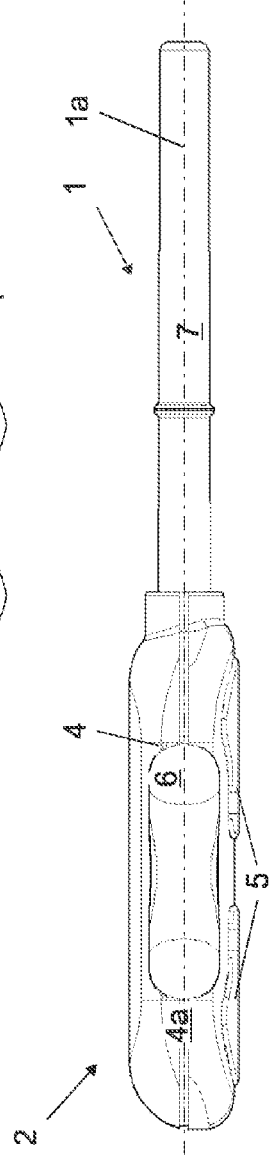

PERINEAL PROBE

FIELD OF THE INVENTION

The present invention relates to a perineal probe, in particular for the treatment of incontinence, of the type comprising a main axis coinciding with the direction of insertion of the probe and a main body, the main body comprising: a continuous lower surface, an upper surface, opposite the lower surface, a lateral surface, extending between the lower surface and the upper surface, comprising two opposite main portions substantially parallel to the main axis and at least two lateral electrodes arranged along said main portions of said lateral surface.

DESCRIPTION OF THE PRIOR ART

Various perineal probes used for different purposes, and in particular for the treatment and re-education of incontinence, are currently known. Said incontinence, whether faecal or urinary, may be caused by many different reasons and factors and be due to the malfunctioning of a plurality of local groups of muscles.

Current methods of re-education for incontinence involve the use of vaginal or anal probes to detect electromyographic activity using EMG (electromyography) or to administer electrical stimulation, or to measure the pressure in the vaginal or anal cavity.

These probes are generally characterised by metal or metallised electrodes, with a circularly symmetric structure. Said probes also come in different types: flat, with unilateral electrodes, or even with a hole in the middle.

However, the perineal probes of the type known in the prior art have some important drawbacks.

In particular, the probes known in the prior art do not permit the precise selection of the groups of muscles to be treated.

As a consequence, said probes may not stimulate the muscles properly, delaying or undoing the benefits of the treatment.

SUMMARY OF THE INVENTION

In this situation the technical purpose of the present invention is to devise a perineal probe able to overcome the drawbacks mentioned above.

Within the sphere of said technical purpose, an important aim of the invention is to provide a perineal probe that permits precise and localised treatments of the groups of muscles to be treated.

A further purpose of the invention is to obtain a simple and economical perineal probe.

The technical purpose and specific aims are achieved with a perineal probe comprising a main axis coinciding with the direction of insertion of the probe and a main body, the main body comprising: a continuous lower surface, an upper surface, opposite the lower surface, a lateral surface, extending between the lower surface and the upper surface and comprising two opposite main portions substantially parallel to the main axis, the perineal probe also comprising at least two lateral electrodes arranged along the main portions of the lateral surface.

BRIEF DESCRIPTION OF THE DRAWINGS

The characteristics and advantages of the invention are clearly evident from the following detailed description of a preferred embodiment thereof, with reference to the accompanying drawings, in which:

FIG. 3 is a scale drawing showing an axonometric view partially from above of the perineal probe according to the invention;

FIG. 4 is a scale drawing of the perineal probe in a view from the bottom;

FIG. 5 is a scale drawing of the perineal probe in a view from above;

FIG. 6 is a scale drawing of the perineal probe in a view from the side; and

FIG. 7 is a scale drawing of the perineal probe in a view from the front.

DESCRIPTION OF THE PREFERRED EMBODIMENTS

Figure 1:
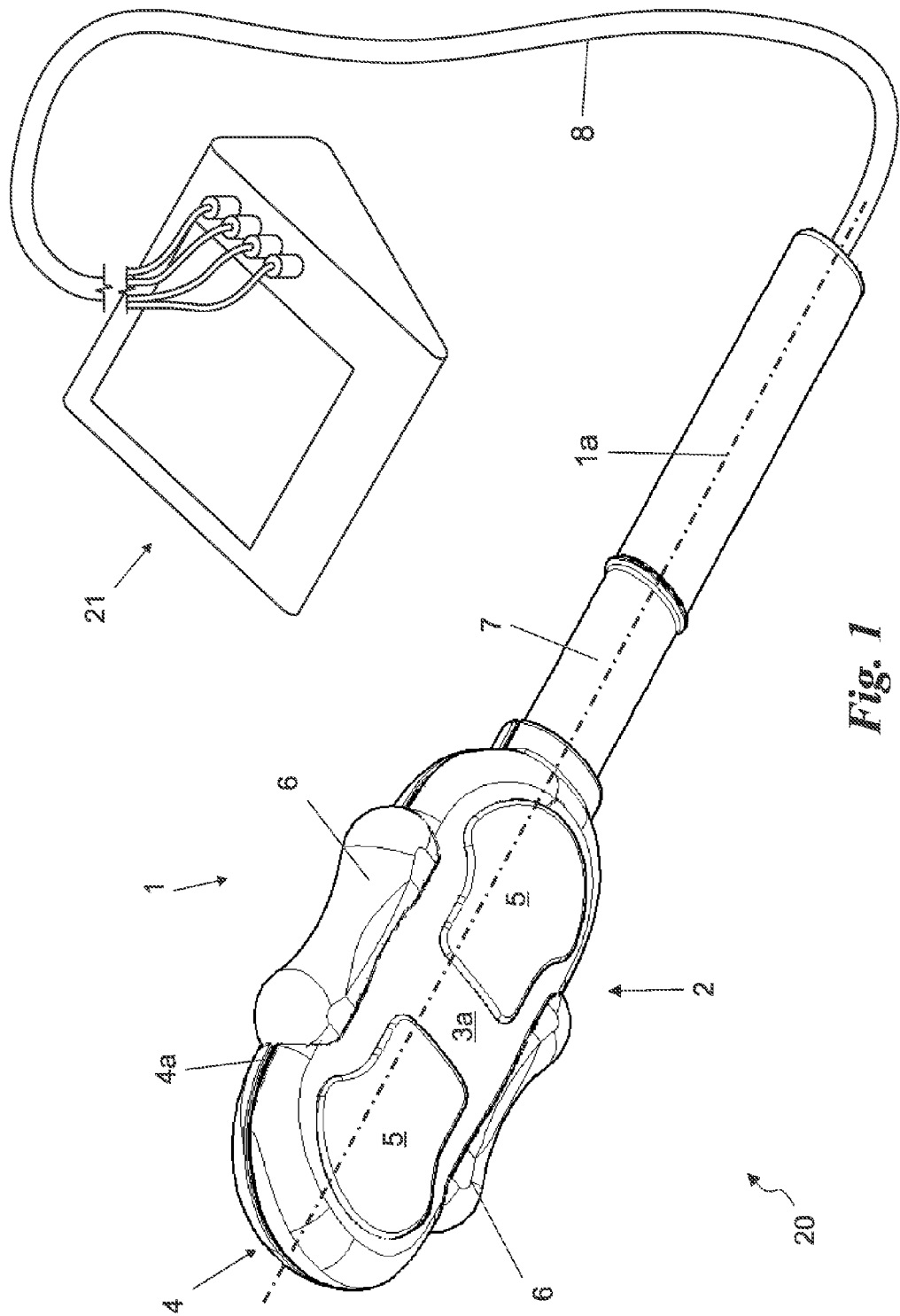
FIG. 1 schematically illustrates the perineal probe connected to control means.

With reference to said drawings, reference numeral 1 globally denotes the perineal probe according to the invention. It is suitable to be connected to control means 21 of said perineal probe 1 suitable to control said probe and/or to receive information from said probe and, if necessary, analyse or simply transmit said information. The perineal probe 1 and the control means 21 constitute an apparatus 20.

The perineal probe 1 comprises a main axis 1a which coincides with the direction in which the probe 1 is inserted into the human body and also with the main direction of extension of the perineal probe 1.

In brief, the probe comprises a main body 2, comprising electrodes, which are described below, and a supporting rod 7, suitable to move and support the main body 2 and extending along said main axis 1a.

The main body 2 comprises a continuous lower surface 3a, an upper surface 3b, opposite the lower surface 3a and a lateral surface 4, extending between the lower surface 3a and the upper surface 3b and comprising two opposite main portions 4a substantially parallel to the main axis 1a.

More in detail, the lower 3a and upper 3b surfaces may be substantially identical. The lower surface 3a is preferably substantially flat and substantially parallel to the main axis 1a. Alternatively it may be convex or otherwise shaped.

It is also substantially continuous, i.e. with no holes or other forms of discontinuity. Clearly, the term substantially refers to the fact that there may be some very slight breaks given by the space between the seats of the electrodes and the electrodes themselves, or between different portions of the body 2, etc.

Furthermore, the lower 3a and upper 3b surfaces have a shape that is elongated, along the plane, and preferably ellipsoidal with two partially rectilinear sides, as illustrated in FIGS. 4 and 5.

The lateral surface 4 joins the two lower 3a and upper 3b surfaces with curved walls, preferably with a substantially constant curvature radius. The length of said main body 2, in the direction of the main axis 1a, is preferably comprised between 3 cm and 7 cm, its width, in the direction perpendicular to the main axis 1a and parallel to the surface 3a, is preferably comprised between 1 cm and 3 cm, while the height, perpendicular to the width and the length, is comprised between 0.3 cm and 2 cm.

The main body 2 also comprises at least two lower electrodes 5, arranged on the lower surface 3a and reciprocally separated along the main axis 1a, and at least two lateral electrodes 6 arranged along the main portions 4a of the lateral surface 4.

Figure 2:
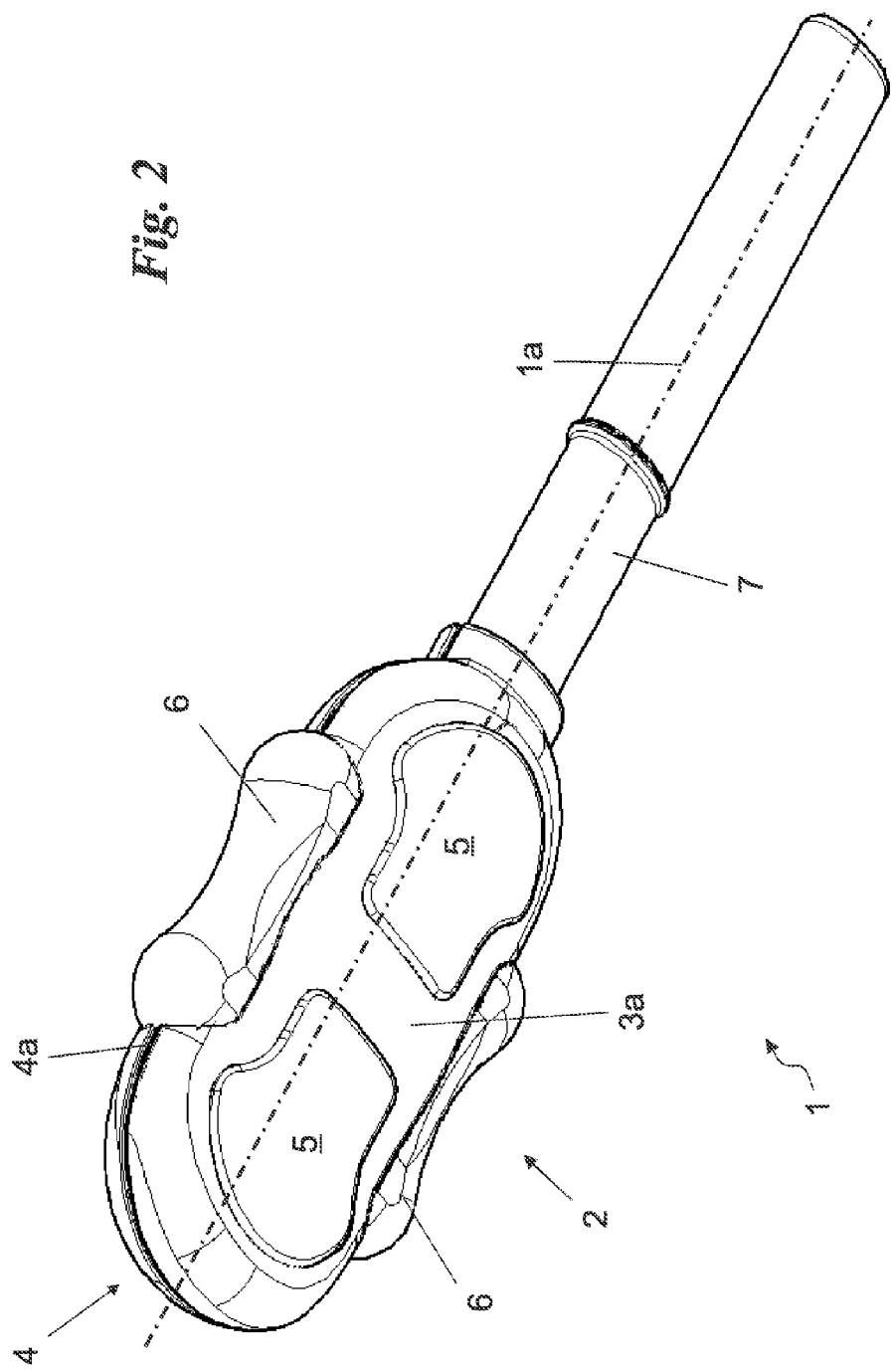
FIG. 2 is a scale drawing showing an axonometric view partially from below of the perineal probe according to the invention.

In particular the lower electrodes 5 have an average diameter comprised between 5 mm and 2 cm and a partially circular and partially rectangular shape, as illustrated in FIGS. 2 and 4. Said lower electrodes 5 are also reciprocally separated by a distance comprised between 0.8 and 0.3 times the size of said average diameter of the lower electrodes 5. Furthermore they are preferably flat and protrude by a length comprised between 0.5 mm and 2 mm from the lower surface 3a. Lastly, the lower electrodes 5 are preferably aligned in parallel with the axis 1a and centred on said axis.

The lateral electrodes 6 extend primarily in a direction parallel to the main axis 1a and are saddle shaped, i.e. having a minimum distance from the main axis 1 in a central portion thereof, as illustrated in FIGS. 2 and 3. They are also of a length comprised between 1 cm and 3 cm and are specularly symmetrical and reciprocally aligned along the main axis 1a. More in detail, the narrowest part of the saddle shape is arranged in correspondence with the space between the lower electrodes 5, as illustrated in FIG. 2.

Moreover, the perineal probe 1 may comprise at least one upper electrode arranged on the upper surface 3b and not illustrated in the accompanying drawings.

The supporting rod 7 mechanically connected to the main body 2 comprises electrical connections 8 connected to the electrodes 5 and 6 and connectable to the control means 21 of the perineal probe 1.

In particular, the connections 8 comprise electrical cables inside the rod 7 and a board with printed circuits or similar components inside the main body 2.

Moreover each single electrode 5 and 6 is provided with an independent electrical connection 8 electrically isolated from the other electrical connections 8. Said solution permits the independent control or receipt of information for each pair of electrodes. The electrical connections 8 also comprise flexible cables that extend beyond the rod 7.

Lastly, the apparatus 20, as described previously, also comprises control means 21 suitable to be connected to the electrical connections 8. They are suitable to control the lower electrodes 5 and the lateral electrodes 6 simultaneously and in a reciprocally independent manner.

Structurally, the main body 2 consists of two shells, preferably partially symmetrical polymeric shells, reciprocally glued or welded. Each shell includes a surface 3a or 3b. Moreover, the lower shell comprises the seats for the lower electrodes 6, consisting of recesses provided with a passage for the electrodes towards the centre of the body 2, where the electrical connections 8 are present. The lower shell also comprises a portion of seats for the lateral electrodes. The upper shell instead comprises the latter.

In the centre of the body 2 there is a printed circuit board PCB which includes the electrical connections 8. Said board also connects the electrodes 5 and 6 preferably by means of joints and/or welding.

The rod 7 is made of a polymeric material over-moulded on the electrical connections 8 consisting of electrical cables.

The perineal probe 1 according to the invention works in the following way.

The physician or his/her assistant inserts the probe into the patient's vaginal or anal cavity and controls it using the control means 21.

In particular, the probe 1 is arranged so that the two branches (rh/lh) of the pubococcygeus muscle rest on the narrowest parts of the lateral saddle-shaped electrodes 6.

In particular, as is known, when any muscle contracts naturally it produces electricity (EMG) which can also be measured using two electrodes arranged at a certain distance along the muscle; vice versa, a muscle contracts artificially when stimulated by an electrical current applied thereto through electrodes arranged along said muscle.

Re-education of incontinence is therefore possible by means of said impulses supplied by the control means 21, transmitted by the electrical connections 8 and by the electrodes 5 and 6. On the contrary, it is also possible to receive signals that monitor any muscular contractions.

In particular, the lower electrodes 5 selectively stimulate the puborectalis muscle, while the lateral electrodes 6 selectively stimulate the pubococcygeus.

Said technical effect is primarily due to the position of the electrodes 5 and 6 and also, to a lesser extent, to their shape and size, their position along the main body 2 and the position of the probe 1 inside the human body, obtained thanks to the saddle shape of the lateral electrodes 6.

The present invention achieves some important advantages.

Thanks to said technical effects it is possible to deliver precise therapies or treatments suited to the patient's problem or physical and muscular structure.

The selective stimulation of different muscles allows the physician to choose different stimulation programs for the electrodes, in particular different in terms of frequency, intensity, waveform, etc. The different electrode stimulations can also be simultaneous.

The invention claimed is:

1. A perineal probe, comprising:
a main axis coinciding with the direction of insertion of said probe and a main body, said main body, comprising:
a continuous lower surface,
an upper surface opposite said lower surface, and
a lateral surface, extending between said lower surface and said upper surface and comprising two opposite main portions substantially parallel to said main axis,
said perineal probe also comprising at least two lateral electrodes arranged along said main portions of said lateral surface configured in that said lower surface is substantially flat and in that it comprises two lower electrodes, having an average diameter comprised between 5 mm and 2 cm, arranged on said lower surface, reciprocally separated along said main axis and aligned in parallel with said main axis and centred on said main axis.

2. The perineal probe as claimed in claim 1, wherein said lower electrodes are reciprocally separated by a distance comprised between 0.8 and 0.3 times the size of said average diameter of said lower electrodes.

3. The perineal probe as claimed in claim 1, wherein the length of said lateral electrodes is comprised between 1 cm and 3 cm.

4. The perineal probe as claimed in claim 1, wherein said lateral electrodes are saddle shaped.

5. The perineal probe as claimed in claim 4, wherein said lateral electrodes are specularly symmetrical and reciprocally aligned along said main axis and wherein said saddle shape comprises a narrowest part in correspondence with said space separating said lower electrodes.

6. The perineal probe as claimed in claim 1, comprising at least one upper electrode arranged on said upper surface.

7. The perineal probe as claimed in claim 1, comprising a supporting rod comprising electrical connections to said electrodes and wherein said electrical connections are connectable to control means of said perineal probe.

8. The perineal probe as claimed in claim 7, wherein each of said electrical connections is specific for a single electrode and is electrically separated from other electrical connections.

9. An apparatus, comprising:
   a perineal probe as claimed in claim 1, and
   control means of said perineal probe,
   wherein said control means are configured to control said lower electrodes and said lateral electrodes simultaneously and in a reciprocally independent manner.

10. The perineal probe as claimed in claim 1, wherein said lower surface is substantially parallel to said main axis.

* * * * *